United States Patent
Stibich et al.

(10) Patent No.: US 9,114,182 B2
(45) Date of Patent: Aug. 25, 2015

(54) GERMICIDAL SYSTEMS AND APPARATUSES HAVING HOLLOW TUMBLING CHAMBERS

(75) Inventors: Mark A. Stibich, Houston, TX (US); Paul R. Stibich, Troy, MI (US)

(73) Assignee: Xenex Disinfection Services, LLC, San Antonio, TX (US)

( * ) Notice: Subject to any disclaimer, the term of this patent is extended or adjusted under 35 U.S.C. 154(b) by 0 days.

(21) Appl. No.: 13/406,725

(22) Filed: Feb. 28, 2012

(65) Prior Publication Data

US 2013/0224086 A1 Aug. 29, 2013

(51) Int. Cl.
*A61L 2/00* (2006.01)
*A61L 2/10* (2006.01)

(52) U.S. Cl.
CPC .............. *A61L 2/10* (2013.01); *A61L 2202/122* (2013.01); *A61L 2202/25* (2013.01)

(58) Field of Classification Search
USPC .......................................................... 34/275
See application file for complete search history.

(56) References Cited

U.S. PATENT DOCUMENTS

| | | | |
|---|---|---|---|
| 2,182,732 A | | 12/1927 | Meyer et al. |
| 2,382,939 A | | 6/1944 | Koch |
| 2,392,095 A | * | 1/1946 | Lemmers .................. 220/2.1 R |
| 2,615,120 A | | 10/1952 | Macksoud |
| 3,418,069 A | | 12/1968 | Decupper |
| 4,005,135 A | | 1/1977 | Helding |
| 4,229,658 A | | 10/1980 | Gonser |
| 4,896,042 A | | 1/1990 | Humphreys |
| 5,144,146 A | | 9/1992 | Wekhof |
| 5,220,734 A | * | 6/1993 | Carver ............................ 34/600 |
| 5,221,139 A | | 6/1993 | Belfer |
| 5,344,433 A | | 9/1994 | Talmore |

(Continued)

FOREIGN PATENT DOCUMENTS

| | | |
|---|---|---|
| CN | 87203475 | 8/1988 |
| CN | 2678651 | 2/2005 |

(Continued)

OTHER PUBLICATIONS

"Couple (v)" Collins English Dictionary—Complete and Unabridged. Harper Collins Publishers 2003. Retrieved from http://www.thefreedictionary.com/couple Nov. 5, 2012.*

(Continued)

*Primary Examiner* — Sean E Conley
*Assistant Examiner* — Donald Spamer
(74) *Attorney, Agent, or Firm* — Mollie E. Lettang; Daffer McDaniel LLP (57) ABSTRACT

Systems are provided which include a disinfection apparatus, a hollow chamber comprising an object entry port, and a means for tumbling objects placed inside the chamber. In some cases, the hollow chamber is configured such that a germicide projected from the disinfection apparatus is transmitted into an interior cavity of the chamber. In other cases, the hollow chamber may include an input port configured for coupling the chamber to the disinfection apparatus such that a germicide generated by the disinfection apparatus is transmitted into the hollow chamber via the input port when the chamber is coupled to the disinfection apparatus. In other cases, the disinfection apparatus may be disposed within the hollow chamber and configured to generate a germicide in the form of a plasma, ultraviolet light, a non-aqueous vapor, a non-aqueous liquid or a gas which is molecularly configured to deactivate or kill microorganisms.

48 Claims, 3 Drawing Sheets

(56) References Cited

U.S. PATENT DOCUMENTS

| | | | |
|---|---|---|---|
| 5,373,430 A | 12/1994 | McDermott | |
| 5,744,094 A | 4/1998 | Castberg et al. | |
| 5,768,853 A | 6/1998 | Bushnell et al. | |
| 5,925,885 A | 7/1999 | Clark et al. | |
| 6,203,060 B1 | 3/2001 | Cech et al. | |
| 6,242,753 B1 | 6/2001 | Sakurai | |
| 6,264,836 B1 | 7/2001 | Lantis | |
| 6,398,970 B1 | 6/2002 | Justel et al. | |
| 6,403,030 B1 | 6/2002 | Horton, III | |
| 6,447,720 B1 | 9/2002 | Horton, III et al. | |
| 6,465,799 B1 | 10/2002 | Kimble et al. | |
| 6,493,087 B1 | 12/2002 | Fabinski et al. | |
| 6,539,727 B1 | 4/2003 | Burnett | |
| 6,566,659 B1 | 5/2003 | Clark et al. | |
| 6,656,424 B1 | 12/2003 | Deal | |
| 6,759,664 B2 | 7/2004 | Thompson et al. | |
| 6,774,382 B2 | 8/2004 | Yoshida | |
| 6,911,177 B2 | 6/2005 | Deal | |
| 6,932,494 B1 | 8/2005 | Burnett et al. | |
| 6,932,903 B2 | 8/2005 | Chang | |
| 6,962,239 B2 | 11/2005 | Shikai et al. | |
| 7,122,115 B2 | 10/2006 | Holt et al. | |
| 7,153,808 B2 | 12/2006 | Iwamoto et al. | |
| 7,175,806 B2 | 2/2007 | Deal et al. | |
| 7,329,026 B1 | 2/2008 | Hayman et al. | |
| 7,371,351 B2 | 5/2008 | Goswami | |
| 7,380,627 B2 | 6/2008 | Huang et al. | |
| 7,423,367 B2 | 9/2008 | Lantis et al. | |
| 7,459,694 B2 | 12/2008 | Scheir et al. | |
| 7,476,006 B2 * | 1/2009 | Hinds | 362/286 |
| 7,498,004 B2 | 3/2009 | Saccomanno | |
| 7,829,867 B2 | 11/2010 | Hlavinka et al. | |
| 8,038,949 B2 | 10/2011 | Horne et al. | |
| 8,142,713 B2 | 3/2012 | Gordon | |
| 8,193,515 B2 | 6/2012 | Kreitenberg | |
| 8,203,126 B2 | 6/2012 | Rocha-Alvarez et al. | |
| 2003/0085631 A1 | 5/2003 | Cech et al. | |
| 2003/0086821 A1 * | 5/2003 | Matthews | 422/29 |
| 2003/0137834 A1 | 7/2003 | Jigamian et al. | |
| 2004/0024278 A1 | 2/2004 | Megerle | |
| 2004/0052702 A1 * | 3/2004 | Shuman et al. | 422/208 |
| 2004/0140782 A1 | 7/2004 | Okabe et al. | |
| 2004/0175290 A1 | 9/2004 | Scheir et al. | |
| 2004/0244138 A1 | 12/2004 | Taylor et al. | |
| 2005/0025662 A1 * | 2/2005 | Lestician | 422/24 |
| 2005/0058013 A1 * | 3/2005 | Warf et al. | 366/98 |
| 2005/0133740 A1 | 6/2005 | Gardner | |
| 2005/0151937 A1 | 7/2005 | Sugitani | |
| 2006/0045817 A1 | 3/2006 | Horne et al. | |
| 2006/0244403 A1 | 11/2006 | Christensson et al. | |
| 2006/0261291 A1 | 11/2006 | Gardner | |
| 2006/0284109 A1 | 12/2006 | Scheir et al. | |
| 2007/0140893 A1 | 6/2007 | McVey et al. | |
| 2007/0188113 A1 | 8/2007 | Okamoto | |
| 2007/0231189 A1 | 10/2007 | Jung et al. | |
| 2007/0231204 A1 | 10/2007 | Hyde et al. | |
| 2007/0253860 A1 | 11/2007 | Schroder | |
| 2008/0056933 A1 | 3/2008 | Moore et al. | |
| 2008/0112845 A1 | 5/2008 | Dunn et al. | |
| 2008/0213128 A1 | 9/2008 | Rudy et al. | |
| 2008/0253941 A1 | 10/2008 | Wichers et al. | |
| 2008/0260601 A1 | 10/2008 | Lyon | |
| 2009/0123343 A1 * | 5/2009 | Kwiatkowski | 422/121 |
| 2009/0129974 A1 | 5/2009 | McEllen | |
| 2009/0191100 A1 | 7/2009 | Deal | |
| 2009/0217547 A1 * | 9/2009 | Kim et al. | 34/275 |
| 2009/0314308 A1 | 12/2009 | Kim et al. | |
| 2009/0323181 A1 | 12/2009 | Andrews et al. | |
| 2010/0026726 A1 | 2/2010 | Fujii et al. | |
| 2010/0044319 A1 | 2/2010 | Engel et al. | |
| 2010/0078574 A1 | 4/2010 | Cooper et al. | |
| 2010/0183476 A1 * | 7/2010 | Lu | 422/21 |
| 2011/0002821 A1 | 1/2011 | Hyde et al. | |
| 2011/0054574 A1 | 3/2011 | Felix | |
| 2011/0206554 A1 | 8/2011 | Anderle et al. | |
| 2011/0215261 A1 | 9/2011 | Lyslo et al. | |
| 2012/0047763 A1 * | 3/2012 | Abramovich et al. | 34/275 |
| 2012/0056102 A1 | 3/2012 | Stanley et al. | |
| 2012/0093688 A1 | 4/2012 | Harmon et al. | |
| 2012/0223216 A1 | 9/2012 | Flaherty et al. | |
| 2012/0313532 A1 | 12/2012 | Stibich et al. | |
| 2012/0315186 A1 | 12/2012 | Davis | |

FOREIGN PATENT DOCUMENTS

| | | |
|---|---|---|
| CN | 201755324 | 3/2011 |
| EP | 0566238 | 10/1993 |
| EP | 2172097 | 4/2010 |
| EP | 2174670 | 4/2010 |
| EP | 2314802 | 4/2011 |
| GB | 2452341 | 3/2009 |
| JP | 57-164062 | 10/1982 |
| JP | 6063107 | 4/1985 |
| JP | 6-63107 | 3/1994 |
| JP | 2003-135581 | 5/2003 |
| JP | 2010-276737 | 12/2010 |
| WO | 94/06482 | 3/1994 |
| WO | 02/058744 | 8/2002 |
| WO | 2007/020282 | 2/2007 |
| WO | 2007/089312 | 8/2007 |
| WO | 2012/142427 | 10/2012 |

OTHER PUBLICATIONS

Partial International Search Report mailed Jun. 13, 2013 for PCT/US2013/028137.

International Search Report & Written Opinion mailed Dec. 4, 2013 for PCT/US2013/028137.

International Preliminary Report on Patentability mailed Apr. 25, 2014 for PCT/US2013/028137.

* cited by examiner

GERMICIDAL SYSTEMS AND APPARATUSES HAVING HOLLOW TUMBLING CHAMBERS

BACKGROUND OF THE INVENTION

1. Field of the Invention

This invention generally relates to germicidal systems and apparatuses and, more specifically, to germicidal systems and apparatuses having hollow tumbling chambers for disinfecting objects.

2. Description of the Related Art

The following descriptions and examples are not admitted to be prior art by virtue of their inclusion within this section.

In general, germicidal systems are designed to subject one or more surfaces and/or objects to a germicide to deactivate or kill microorganisms residing upon the surface/s and/or object/s. Applications of germicidal systems include but are not limited to sterilization, object disinfection, and room/area decontamination. Examples of area/room decontamination systems are those used in hospital rooms to disinfect the objects therein and those used in agricultural operations, such as those which are used to breed and/or farm animals. Examples of sterilizing systems are those used for sterilizing surgical tools, food or pharmaceutical packaging. A challenge in many applications is accessing all surfaces of an object to insure thorough disinfection of the object. In particular, some germicidal systems may only effectively treat surfaces which are facing the germicidal system and, thus, surfaces not facing the system may not be disinfected adequately.

Furthermore, surfaces of an object which are in contact with a surface of another object, such as the surface of an object touching the surface of a table or surfaces of a plurality of objects stacked upon each other are hidden from exposure and, thus, such surfaces are not disinfected. Objects which are particularly susceptible for being in contact with other objects are those which are relatively small and portable. Furthermore, such objects are often handled by humans, making them more likely to have germs on their surfaces. Some germicidal systems include trays for objects to be positioned on such that access to surfaces of the objects may be manipulated. Such trays, however, are labor and time intensive in that the objects must be carefully positioned to avoid overlapping the objects and, further, that the objects must be turned over during a disinfection process to insure disinfection of surfaces that were originally placed in contact with the trays.

Accordingly, it would be advantageous to develop a germicidal system that can effectively access all surfaces of objects during a disinfection process with minimal labor involved and minimal interruptions to the disinfection process.

SUMMARY OF THE INVENTION

The following description of various embodiments of systems and apparatuses is not to be construed in any way as limiting the subject matter of the appended claims.

Embodiments of systems include a disinfection apparatus, a chamber comprising a hollow interior and a loading port for entry of objects into the hollow interior, and a means for tumbling objects placed inside the chamber. In some cases, the disinfection apparatus is configured to project a germicide exterior to the disinfection apparatus and the hollow chamber is configured such that the germicide projected from the disinfection apparatus is transmitted into an interior cavity of the hollow chamber. In other cases, the hollow chamber may include an input port configured for coupling the chamber to the disinfection apparatus such that a germicide generated by the disinfection apparatus is transmitted into the hollow interior of the chamber via the input port when the chamber is coupled to the disinfection apparatus.

Embodiments of apparatuses include a hollow chamber with a loading port and a device disposed within the hollow chamber which is configured to generate a germicide within the hollow chamber, wherein the germicide is in the form of a plasma, ultraviolet light, a non-aqueous vapor, a non-aqueous liquid, or a gas which is molecularly configured to deactivate or kill microorganisms. In addition, the apparatuses include a means for causing objects placed inside the hollow chamber to tumble within the hollow chamber.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
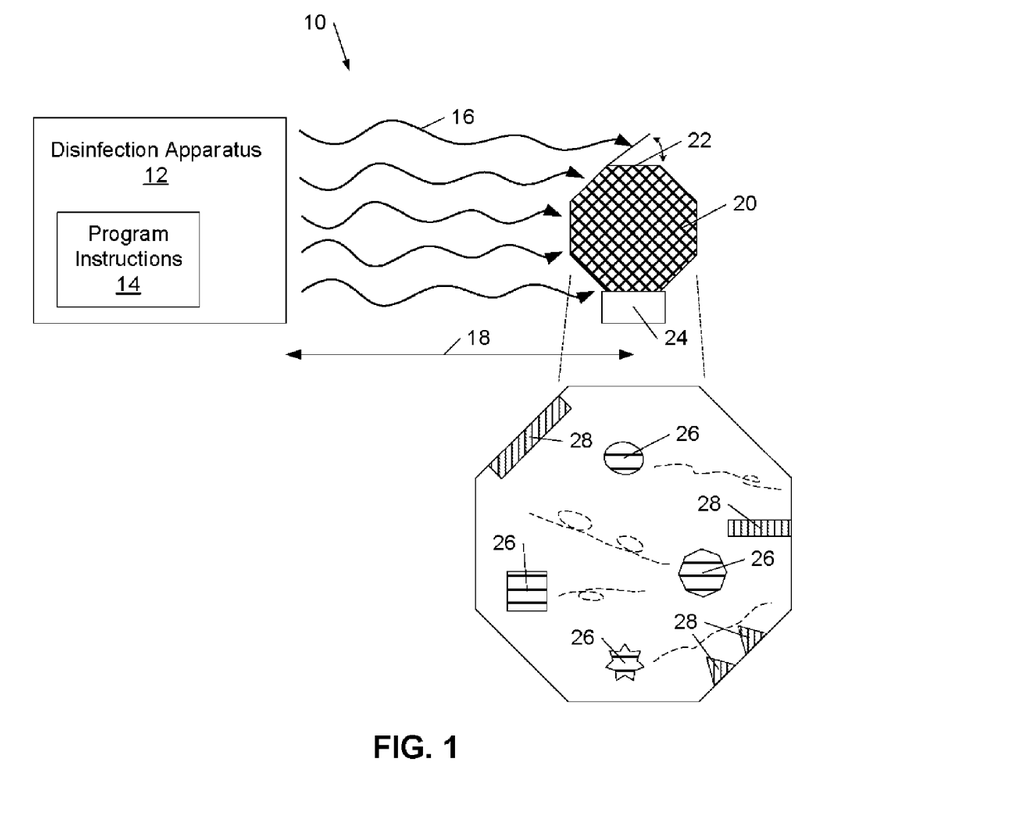
FIG. 1 is a schematic drawing of a system comprising a disinfection apparatus and hollow tumbling chamber spaced in proximity thereto.
Figure 2:
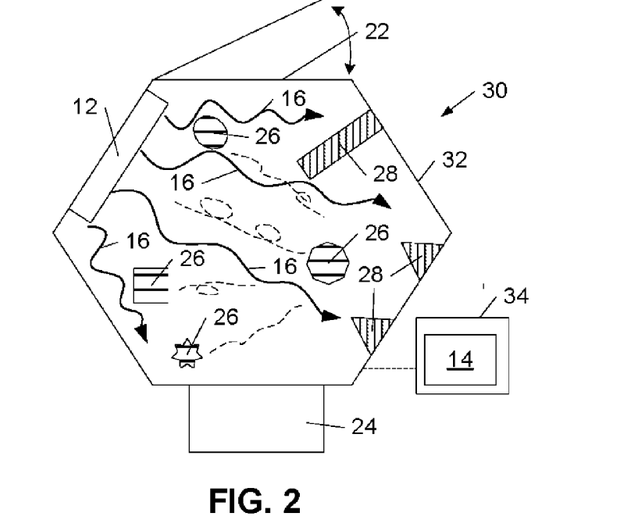
FIG. 2 is a schematic drawing of an apparatus having a germicidal device disposed within a hollow tumbling chamber.
Figure 3:
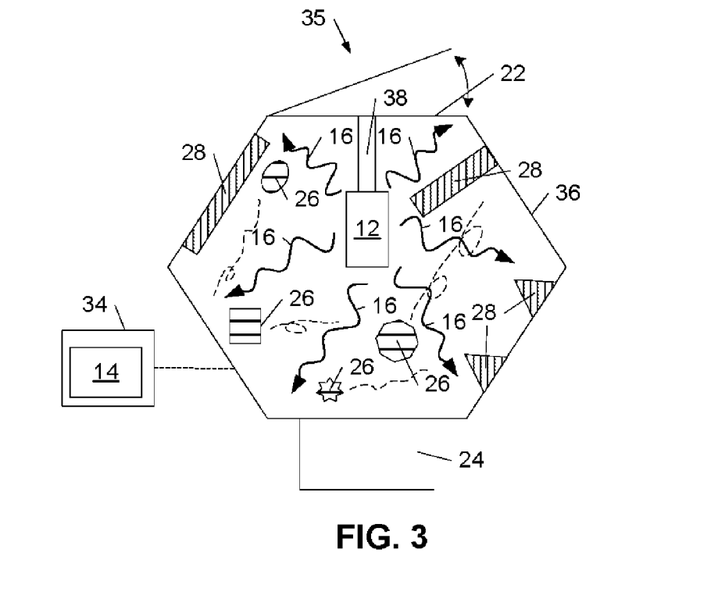
FIG. 3 is a schematic drawing of another apparatus having a germicidal device disposed within a hollow tumbling chamber.
Figure 4:
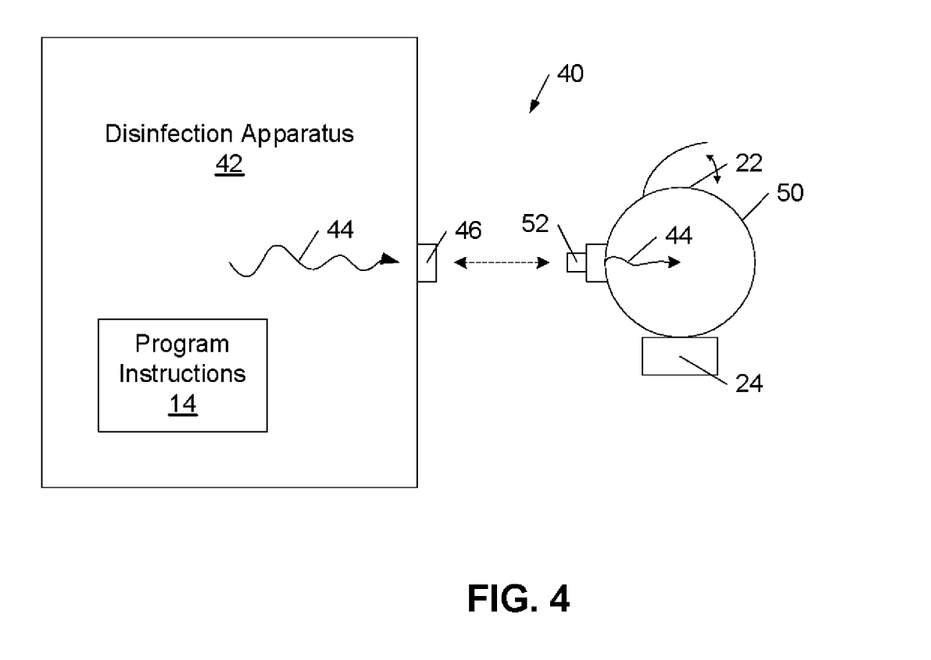
FIG. 4 is a schematic drawing of a system with a hollow tumbling chamber comprising an input port which is configured for coupling to a disinfection apparatus of the system.

Turning to the drawings, FIGS. 1-4 depict examples of germicidal systems and apparatuses which include hollow tumbling chambers for disinfecting objects. In particular, FIG. 1 depicts system 10 including hollow chamber 20 configured such that a germicide generated and projected from disinfection apparatus 12 is transmitted into an interior cavity of the hollow chamber. FIGS. 2 and 3 respectively show apparatuses 30 and 35 having germicidal device 12 disposed within hollow chambers 32 and 38. Furthermore, FIG. 4 illustrates system 40 including hollow chamber 50 with input port 52 configured for coupling to disinfection apparatus 42 such that a germicide generated by disinfection apparatus 42 may be transmitted into the interior of the hollow chamber via the input port when the chamber is coupled to the disinfection apparatus. As shown in FIGS. 1-4, each of the systems and apparatuses include means 24 for tumbling objects placed inside the hollow chambers. Distinctions of the systems and apparatuses depicted in FIGS. 1-4 are described in more detail below in reference to the different figures. As set forth below, alternative configurations of systems and apparatuses may be considered and, thus, the systems and apparatuses described herein are not limited to the depictions in FIGS. 1-4. Furthermore, it is noted that the drawings are not necessarily drawn to scale.

Each of the systems and apparatuses described herein includes a disinfection device. The disinfection device may be any device or apparatus configured to generate a dispersible germicide. In particular, the disinfection device may be any device or apparatus configured to generate a germicide in form of a liquid, a vapor, a gas, a plasma or ultraviolet light. As used herein, the term "germicide" refers to an agent for deactivating or killing microorganisms, particularly disease carrying and/or disease producing microorganisms (a.k.a, germs). The term "kill," as used herein, means to cause the death of an organism. In contrast, the term "deactivate," as used herein, means to render an organism unable to reproduce without killing. As such, a germicide which is configured to deactivate a microorganism, as used herein, refers to an agent which renders a microorganism unable to reproduce but leaves the organism alive.

In some cases, a disinfection device of the systems and apparatuses described herein may be configured to generate a liquid, vapor, gaseous or plasma germicide that is molecularly configured to deactivate and/or kill microorganisms. As used herein, the phrase "molecularly configured" refers to the elemental composition of a substance (i.e., the number and type of atoms making up a substance) to impart the function stated after the phrase. In some embodiments, the functionality of a liquid, vapor, gaseous or plasma germicide to deactivate and/or kill a microorganism may be attributed to the elements constituting the germicide and, thus, such germicides may be referenced as being molecularly configured to deactivate and/or kill microorganisms. This is in contrast to liquid, vapor, gaseous or plasma germicides which impart their deactivation and/or killing functionality by the manner in which they are used. For example, boiling water and steam are often effective sterilizing agents due to the temperature at which they are employed rather than their molecular composition. An example of a gaseous germicide which deactivates or kills microorganisms by the manner in which it is used is air at a very high temperature. Furthermore, the germicidal effectiveness of some plasma germicides is primarily due to the presence and activity of charged particles making up the plasma rather than the molecular composition of the charged particles.

An example of a gaseous germicide that is molecularly configured to kill microorganisms is ozone. Examples of plasmas germicides that are molecularly configured to deactivate or kill microorganisms are those that employ or generate reactive oxygen species. Examples of liquid and vapor germicides that are molecularly configured to deactivate or kill microorganisms include liquid and vapor disinfection solutions having a principle disinfection agent such as but not limited to bleach, hydrogen peroxide, chlorine, alcohol, quaternary ammonium compounds or ozone. In any of such cases, the liquid and vapor germicides may be aqueous or non-aqueous. It is noted that although disinfection devices which are configured to generate a liquid, vapor, gaseous or plasma germicide that is molecularly configured to deactivate or kill microorganisms are discussed in detail above, the systems and apparatuses considered herein may, in some embodiments, include a disinfection device configured to generate a liquid, vapor, gaseous or plasma germicide which imparts its deactivation or killing functionality by the manner in which it is used, such as via boiling water, steam or heated air. In any case, examples of apparatuses which may be configured to disperse liquid, vapor, gaseous, or plasma germicides include but are not necessarily limited to liquid sprayers, foggers, plasmas torchers and misting systems including wet and dry mist systems. As used herein, the term "mist" refers to a suspension of minute globules of a liquid in a gas. For use herein, a germicidal mist is categorized as a liquid germicide.

As noted above, the disinfection device of the systems and apparatuses described herein may, in some embodiments, be a device or apparatus configured to generate a germicide in form of ultraviolet light. In such cases, the disinfection device may generally include a discharge lamp for generating the ultraviolet light. The term "discharge lamp" as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the discharge lamps which may be considered for the disinfection devices described herein include gas-discharge lamps as well as surface-discharge lamps.

Discharge lamps may be further characterized by the type of gas/es employed and the pressure at which they are operated. The discharge lamps which may be considered for the disinfection devices described herein may include those of low pressure, medium pressure and high intensity. In addition, the gas/es employed may include helium, neon, argon, krypton, xenon, nitrogen, oxygen, hydrogen, water vapor, carbon dioxide, mercury vapor, sodium vapor and any combination thereof. In some embodiments, various additives and/or other substances may be included in the gas/es. In any case, the discharge lamps considered for the disinfection devices described herein may be of any size and shape, depending on the design specifications of the apparatuses. Moreover, the discharge lamps considered for the disinfection devices described herein may include those which generate continuous light and those which generate light in short durations, the latter of which are often referred to as flashtubes or flashlamps. Flashtubes or flashlamps that are used to supply recurrent pulses of light are often referred to as pulsed light sources.

A commonly used gas-discharge lamp used to produce continuous light is a mercury-vapor lamp, which may be considered for some of the disinfection devices described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the disinfection devices described herein is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm). In addition, a xenon flashtube can provide relatively sufficient intensity in the spectrum which is known to be optimally germicidal (i.e., between approximately 260 nm and approximately 265 nm). Moreover, a xenon flashtube generates an extreme amount of heat, which can further contribute to the deactivation and/or killing of microorganisms.

Although they are not readily available on the commercial market to date, a surface-discharge lamp may be considered for some of the disinfection devices described herein as noted above. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, offer greater UV efficiency as well as longer lamp life as compared to xenon flashtubes. It is noted that the aforementioned descriptions and comparisons of a mercury-vapor lamp, a xenon flashlamp, and a surface discharge lamp in no way restrict the disinfection devices described herein to include such lamps. Rather, the aforementioned descriptions and comparisons are merely provided to offer factors which one skilled in the art may contemplate when selecting a discharge lamp for an ultraviolet disinfection device, particularly depending on the objective and application of the device.

In any case, an apparatus configured to generate a germicide in form of ultraviolet light may include a support structure for supporting a discharge lamp. In some cases, the discharge lamp may extend beyond an exterior surface of the support structure. A benefit of having a discharge lamp extend beyond an exterior surface of a support structure is that ultraviolet light emitted from the discharge lamp encircles an exterior surface of the apparatus. In particular, the extension of a discharge lamp beyond an exterior surface of a support structure innately causes ultraviolet light emitted from discharge lamp to encircle the lamp housing, which comprises an exterior surface of the apparatus. Depending on the height of a support structure as well as the height of a discharge lamp assembly, the extension of a discharge lamp beyond an exterior surface of a support structure may cause ultraviolet light emitted from the discharge lamp to encircle support structure as well. Further yet, the extension of a discharge lamp beyond an exterior surface of a support structure may, in some embodiments, cause ultraviolet light to propagate to a region which is between approximately 2 feet and approximately 4 feet from a floor in which an apparatus is arranged, which as described below may be considered a high touch zone in a room. In yet other cases, although the suspension of a discharge lamp above a support structure may be beneficial for distributing light around an apparatus, the placement of a discharge lamp is not necessarily so limited. In particular, a discharge lamp may alternatively be arranged upon a support structure or may be partially disposed with a support structure. In such cases, the apparatus may optionally include a reflector system configured to redirect ultraviolet light propagating away from the support structure to encircle an exterior surface of the apparatus.

The term encircle as used herein refers to the formation of a continuous circle around an object. The term is not restricted to embodiments of surrounding an entirety of an object or even a major portion of an object. Thus, the phrasing that an ultraviolet disinfection apparatus may be configured such that ultraviolet light encircles an exterior surface of the apparatus refers to the formation of a continuous ring of ultraviolet light around at least some exterior portion of the apparatus.

In some embodiments, an ultraviolet disinfection apparatus may be configured to move a discharge lamp assembly in and out of a support structure. Such a configuration may be advantageous for protecting the discharge lamp assembly from damage while the disinfection apparatus is not in use and, particularly, in transport. In other embodiments, an ultraviolet disinfection apparatus may be configured to move a discharge lamp assembly while the disinfection apparatus is in operation and, in some cases, while the discharge lamp is emitting light. In particular, in some embodiments, it may be advantageous to move the discharge lamp assembly while the ultraviolet disinfection apparatus is in operation to aid in the distribution of ultraviolet light within a room in which the disinfection apparatus is arranged. Several manners of effecting movement of the discharge lamp assembly may be considered. For example, an ultraviolet disinfection apparatus may have linear actuators to move the discharge lamp assembly or have fixed rails along which the discharge lamp assembly may move. In any case, other optional features for an ultraviolet disinfection apparatus include wheels and a handle to affect portability for the apparatus. In addition or alternatively, an ultraviolet disinfection apparatus may include a room occupancy sensor as an optional safety mechanism. In particular, an ultraviolet disinfection apparatus may be configured to determine whether people are present in the room, such as by motion detection or photo recognition. In addition or alternatively, an ultraviolet disinfection apparatus may include a central processing unit to execute program instructions associated with operations of the apparatus. Any of such optional features (i.e. linear actuators, fixed rails, wheels, a handle, a room occupancy sensor and a central processing unit) may be disposed within or on a support structure of the ultraviolet disinfection apparatus which supports the discharge lamp of the apparatus.

In addition to being configured to generate ultraviolet light, a discharge lamp of an apparatus may be configured to generate other ranges of light, such as but not limited to visible light. In some of such cases, it may be advantageous to attenuate the visible light, particularly if (but not necessarily so limited) the generated visible light is very bright and/or distracting. For instance, xenon flashlamps generate pulses of a broad spectrum of light similar to the spectrum of sunlight, but the intensity of the visible light is up to 20,000 times higher than that of sunlight. As such, an apparatus which includes a discharge lamp to generate a germicide may, in some embodiments, include an optical filter configured to attenuate visible light. In some cases, an ultraviolet disinfection apparatus may include an optical filter configured to attenuate light in a majority portion of the visible light spectrum, greater than 75% of the visible light spectrum, or the entire visible light spectrum. In other embodiments, however, the optical filter may be configured to attenuate light in less than a majority portion of the visible light spectrum. In any case, the optical filter may be configured to attenuate a majority amount of light in a given portion of the visible light spectrum and, in some cases, greater than 75% or all light in a given portion of the visible light spectrum.

Since disinfection apparatuses having a discharge lamp are configured for ultraviolet light exposure, the optical filter must pass ultraviolet light in addition to attenuating visible light. As such, in some cases, the optical filter may be visible light band-stop filter. In other embodiments, however, the optical filter may be an ultraviolet band-pass filter. In either case, the optical filter may be configured to pass a majority amount of light in a given portion of the ultraviolet light spectrum and, in some embodiments, greater than 75% or all light in a given portion of the ultraviolet light spectrum. In some cases, the given portion of the ultraviolet light spectrum may be a majority portion of the ultraviolet light spectrum, greater than 75% of the ultraviolet light spectrum, or the entire ultraviolet light spectrum. In other embodiments, however, the given portion of the ultraviolet light spectrum may be less than a majority portion of the ultraviolet light spectrum. In some embodiments, the optical filter may be specifically configured to pass light in a specific portion of the ultraviolet spectrum. For example, the optical filter may be configured to pass light in a majority portion, greater than 75%, or the entire portion of the germicidal UV spectrum (i.e., approximately 200-320 nm). In addition or alternatively, the optical filter may be configured to pass light in a majority portion, greater than 75%, or the entire portion of the ultraviolet light spectrum known to be optimally germicidal (i.e., approximately 260-265 nm).

An exemplary optical filter glass material which may be used as an optical filter for an ultraviolet disinfection apparatus is Schott UG5 Glass Filter which is available from SCHOTT North America, Inc. of Elmsford, N.Y. Schott UG5 Glass Filter attenuates a majority portion of the visible light spectrum while allowing approximately 85% of ultraviolet light in a range of approximately 260 nm to approximately 265 nm to pass. Other optical filter glass materials with similar or differing characteristics may be used as well, depending on the design specifications of an apparatus. In other cases, an optical filter considered for ultraviolet disinfection apparatuses may be a film having any of the optical characteristics described above. In such embodiments, the film may be disposed on an optically transparent material, such as quartz. In other embodiments, an optical filter considered for an ultraviolet disinfection apparatus may be a combination of an optical filter glass material and a film disposed thereon, each of which is configured to attenuate visible light. The term optical filter glass material used herein refers to a material designed to influence the spectral transmission of light by either blocking or attenuating specific wavelength spectrums. In contrast, the term optically transparent used herein refers to a material which allows light to pass through without substantial blockage or attenuation of a specific wavelength spectrum. Quartz is a well known optically transparent material. The term film as used herein refers to a thin layer of a substance and is inclusive to the term coating which refers to a layer of a substance spread over a surface. Films considered for the optical filters described herein may be in solid or semi-solid form and, thus, are inclusive to solid substances and gels.

Two other components that each of the systems and apparatuses described herein include are a hollow chamber and a means for providing tumbling action to objects placed inside the hollow chamber. The hollow chamber may be of any configuration (i.e., size, shape, material constructions, etc.), depending on the design specifications of the systems and apparatuses and, particularly, the size and materials of the objects to be disposed within the hollow chamber. For example, if heavy, hard and/or pointy objects are to be disposed within the hollow chamber, the hollow chamber may be constructed to withstand the bombardment of the objects against the interior surface of the hollow chamber. Alternatively, if relatively light and/or soft objects are to be disposed within the hollow chamber, the hollow chamber may be constructed for less vigor. As such, it is contemplated that the hollow chambers considered herein may include rigid and/or pliable construction. In general, a rigid construction refers to a design which is not flexible, while a pliable construction refers to a design which is flexible, such as be being bendable and/or collapsible.

In any case, the hollow chambers considered herein may, in some embodiments, include an antimicrobial material, particularly but not limited to an interior surface of the chamber. Examples of antimicrobial materials include but are not limited to particular alloys of copper and silver. The antimicrobial material may, in some cases, be a coating or a film on a structural component of the hollow chamber. In yet other embodiments, the antimicrobial material may be a structural component of the hollow chamber. In any case, the hollow chambers considered herein, particularly but not limited to the interior surface of the chamber, may additionally or alternatively include one or more materials which are adhesion resistant, such as, for example, polytetrafluoroethylene (PTFE). In any case, the hollow chamber includes a loading port for loading objects therein. The loading port may be of any configuration (i.e., shape, size, design, etc.) and may generally be closable such that objects placed inside the hollow chamber do not fall out during operation. In some cases, the hollow chamber may include one or more ledges along walls on the interior of the chamber to aid in effecting tumbling action of the objects disposed within the chamber. If multiple ledges are used, they may be of the same dimensions, different dimensions or a combination thereof.

As noted above, each of the systems and apparatuses described herein includes a means for providing tumbling action to objects placed inside the hollow chamber. Examples of such tumbling means include but are not limited to a rotation motor, pneumatics or a vibrator. In some cases, the means for providing tumbling action may include an electromechanical, hydraulic or rotational shaft. In some embodiments, the means for providing tumbling action to objects placed inside the hollow may include means for moving the chamber itself, such as by rotating, oscillating, or simply displacing the chamber in one or more directions repeatedly. In other embodiments, the means for providing tumbling action may not move the hollow chamber. For example, pneumatics may be used to provide tumbling action without having to move the hollow chamber. In yet other embodiments, a hollow chamber may include an inner sleeve and the means for providing tumbling action may include moving the inner sleeve without having to move the chamber as a whole. In some cases, the means for providing tumbling action may include a plurality of means for doing so, including but not limited to the aforementioned means. As used herein, the phrase "tumbling action" refers to movements which include traveling end over end and/or tossing about in a three-dimensional manner, particularly in an erratic manner. In particular, the tumbling means considered for the systems and apparatuses described herein are configured such that objects within the hollow chamber are suspended at least for a brief time and, in some cases, a majority of time during operation of the systems and apparatuses. In this manner, all surfaces of an object are spaced apart from the interior walls of the hollow chamber for at least some if not a majority of the processing time.

Furthermore, the tumbling means provided for the systems and apparatuses described herein is preferably configured to induce sufficient movement among the objects placed inside the hollow chamber such that each of the objects are spaced apart from each other for at least a brief time and, in some cases, a majority of time during operation of the systems and apparatuses. In this manner, all surfaces of an object may be exposed to the germicide dispersed into the hollow chamber. In some cases, such functionality may be dependent on how full the hollow chamber is (i.e., the amount of area which is occupied by the objects). In particular, it may be advantageous in some embodiments to limit the amount the hollow chamber is occupied by objects such that sufficient tumbling may occur. In view thereof, the hollow chamber may, in some embodiments, include a threshold fill line, indicating a maximum level at which the hollow chamber should be filled with objects. In general, the location of a threshold fill line may vary among systems and applications and may be dependent on the configuration of the objects to be treated. An exemplary location of a threshold fill line may be a place on a chamber which is approximate to half the volume of the chamber from its base, but other locations may be suitable as well.

The objects which may be placed into the hollow chamber of the systems and apparatuses described herein may be of any configuration (i.e., shape, size, weight, material, construction, etc.) and may particularly depend on the configuration of the hollow chamber and the environment in which the systems and apparatuses are being employed. In general, objects which are relatively small and portable may be particularly suitable. For example, as set forth below, in some cases the systems and apparatuses described herein may be used in hospital rooms. In such embodiments, objects which may be considered for treatment in the hollow chambers of the systems and apparatuses described herein may include supplies which are kept within a hospital room for ready access, such as but not limited to bandages, cotton swabs and alcohol wipes. In particular, such items are generally stored together in contact with each other and, thus, may not be adequately disinfected unless they are individually treated. Other non-medical items may be considered for treatment in the hollow chambers as well, such as but not limited to pens, pads of paper, and pamphlets. In any case, objects of the same configuration or of different configurations may be placed inside the hollow chamber for a given treatment process.

An optional feature that the systems and apparatuses described herein may include is a storage medium comprising processor executable program instructions, particularly program instructions for varying operational parameters of the tumbling action means while the disinfection apparatus is in operation. In general, the term "storage medium", as used herein, may refer to any electronic medium configured to hold one or more set of program instructions, such as but not limited to a read-only memory, a random access memory, a magnetic or optical disk, or magnetic tape. In some embodiments, the disinfection device or the germicidal apparatus as a whole may include the storage medium. In other cases, the storage medium may be a separate component. The term "program instructions", as used herein, may generally refer to commands within a program which are configured to perform a particular function, such as receiving input, recording receipts of signals, determining when and/or whether to allow a device to start an operation, and sending signals to start and/or end operation of a device. Program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. Program instructions implementing the processes described herein may be transmitted over on a carrier medium such as a wire, cable, or wireless transmission link.

As noted above, FIGS. 1-4 illustrate different examples of germicidal systems and apparatuses which include hollow tumbling chambers for disinfecting objects. Each of the systems and apparatuses include a disinfection device, a hollow chamber and a means for providing tumbling action to objects placed inside the hollow chamber. The configuration of each of these devices may generally include the characteristics noted above for each item. The characteristics are not reiterated for the descriptions of FIGS. 1-4 for the sake of brevity. The systems and apparatuses shown in FIGS. 1-4 offer distinguishing features, each of which is described in more detail below. It is noted that features depicted in FIGS. 1-4 with the same configurations are denoted with the same reference numbers and the descriptions of such features are not reiterated for each figure for the sake of brevity.

Turning to FIG. 1, system 10 is shown including hollow chamber 20 configured such that a germicide generated and projected from disinfection apparatus 12 is transmitted into an interior cavity of the hollow chamber. The configuration of hollow chamber 20 to allow such activity is based on spacing 18 of the hollow chamber from disinfection apparatus 12 as described in more detail below as well as the construction of hollow chamber 20, particularly whether it has perforations and/or is constructed of one or more optically transparent materials. In some cases, hollow chamber 20 may include multiple perforations (i.e., through holes) arranged along its exterior surface providing access to its interior cavity, particularly for germicide 16. The perforations may be of any size, shape and density, depending on the size and shape of the objects to be placed therein. In general, it would be advantageous for the perforations to be as large as possible barring the possibility of an object falling through or getting stuck in the perforations. In addition, it would be advantageous to maximize the density of the perforations to maximize the amount of germicide transmitted into the chamber. In any case, the perforations may be of the same dimensions, different dimensions or a combination thereof. As noted above, the hollow chambers considered herein may include rigid and/or pliable construction, depending on the objects to be disposed within the hollow chamber. One type of pliable construction which may be considered when hollow chamber 20 includes perforations is a Hoberman sphere design, but other pliable constructions may be employed as well. Alternatively, hollow chamber 20 may have a rigid construction.

It is noted that alternative configurations of hollow chambers may be considered for system 10 when disinfection apparatus 12 includes an ultraviolet light disinfection apparatus. In particular, hollow chamber 20 may, in some embodiments, additionally or alternatively include one or more optically transparent materials to permit transmission of ultraviolet light into the interior of the hollow chamber. In some cases, hollow chamber 20 may include panes of one or more optically transparent materials in place of the perforations described above. In yet other embodiments, an entirety of the chamber walls may be constructed of one or more optically transparent materials. The design selection among these options may depend on the strength and durability needs of the chamber, particularly relating to the configuration of the objects to be placed therein. In particular, narrow strips of a different material (e.g., metal or plastic) along side panes of an optical material may offer a structural support for the chamber which is stronger than what may be obtained if the chamber is constructed only of an optical material. In any case, an example of an optically transparent material which may be used for these embodiments is quartz, but other optically transparent materials may be used. It is noted that use of optically transparent materials for hollow chamber 20 is not required when disinfection apparatus 12 includes an ultraviolet light disinfection device. Rather, such a configuration is optional and, thus, hollow chamber 20 may not, in some embodiments, include optically transparent materials for the transmission of ultraviolet light to the interior of the chamber when disinfection device 12 includes an ultraviolet light disinfection device. In other cases, hollow chamber 20 may include perforations and one or more optically transparent materials for the passage of germicides into its interior. Such a configuration may offer versatility in the type of disinfection device which system 10 may employ and, thus, such configuration is not limited to use with ultraviolet light disinfection devices.

As noted above, the hollow chambers considered for the systems and apparatuses described herein may be of any configuration, including any shape or size. As such, the shape of hollow chamber 20 should not be limited to the octagonal shape depicted in FIG. 1 nor the hexagonal shapes of the hollow chambers depicted in FIGS. 2 and 3 nor the spherical shape of the hollow chamber depicted in FIG. 4. Furthermore, the size of hollow chamber 20 should not be limited to its size relative to disinfection apparatus 12 in FIG. 1 nor the size relationship depicted FIGS. 2-4 between the hollow chambers and disinfection devices shown those figures. As noted above, the features in the drawings are not necessarily drawn to scale and, thus, the size of the features should not be limited by their illustration in the drawings. Furthermore, it is noted that sizes of disinfection devices vary widely, particularly in regard to the type of germicide a disinfection device is configured to generate as well as the application in which a disinfection device is to be used. Thus, the disinfection devices of the systems and apparatuses shown in FIGS. 1-4 should not be restricted by their size relative to other features of the systems and apparatuses.

As further noted above, the hollow chambers considered herein include a loading port for entry of objects into the interior cavity of the chambers. As shown in FIG. 1, hollow chamber 20 includes loading port 22 in an exemplary position at the top of the chamber with a swinging door. The loading port may be alternatively positioned along other locations of chamber 20 and/or may include other door configurations, such as a sliding or removable door. As further shown in FIG. 1, system 10 includes means 24 for providing tumbling action for objects placed inside hollow chamber 20. An interior view of hollow chamber 20 is shown in FIG. 1, particularly showing objects 26 tumbling therein via the dotted lines trailing the objects. Reference is made to the definition of the phrase "tumbling action" noted above as well as the configurations and examples noted for the tumbling means considered for the systems and apparatuses described herein. Such information is referenced for means 24, but is not reiterated for the sake of brevity.

In some embodiments, system 10 may include a storage medium comprising program instructions which are executable by a processor for varying operational parameters of means 24 while disinfection apparatus 12 is in operation. As shown in FIG. 1, disinfection apparatus 12 may be the storage medium in some cases. In other embodiments, the storage medium may be a separate component of system. In yet other cases, hollow chamber 20 may be the storage medium for such program instructions. As further shown in FIG. 1, the interior of hollow chamber 20 may include ledges 28 along its sidewalls. As noted above, ledges may aid in effecting tumbling action of the objects disposed within the chamber. Although FIG. 1 illustrates hollow chamber 20 including multiple ledges with different dimensions, multiple ledges having the same dimensions may be considered. In yet other cases, hollow chamber 20 may include a single ledge or may be void of ledges.

As shown in FIG. 1, disinfection apparatus 12 is configured to project germicide 16 exterior to the disinfection apparatus. In this manner, germicide 16 may be transmitted into hollow chamber 20 when the chamber is arranged in proximity to disinfection apparatus 12. In general, distance 18 denoting the spacing between hollow chamber 20 and disinfection apparatus 12 in FIG. 1 may vary among systems, depending on the germicide projection characteristics of disinfection apparatus 12. An exemplary distance may be less than approximately 5 feet and, more specifically, less than approximately 2 feet, but longer distances may be employed. In any case, system 10 may, in some embodiments, be disposed within a housing such that the germicide may be contained. Such a configuration may be desirable when it is desirable to prevent projection of the germicide into the environment and/or prevent human exposure to the germicide. In other embodiments, system 10 may not be contained within a housing. For example, in some cases, system 10 may be used for room disinfection. As used herein, the term room disinfection refers to the cleansing of a bounded area which is suitable for human occupancy so as to deactivate, destroy or prevent the growth of disease-carrying microorganisms in the area. An example of an application in which a room disinfection system may be used is the disinfection of hospital rooms or any other rooms or areas which may be particularly susceptible to being contaminated with disease-carrying microorganisms.

In cases in which system 10 is used as a room disinfection system, disinfection apparatus 12 may be specifically configured to disperse germicide 16 to a specific region of a room. For example, in some embodiments, disinfection apparatus 12 may be configured to disperse germicide 16 to a region of a room suspected to have a high concentration of germs. An example of a region that is often considered to have a high concentration of germs is a "high touch" region of a room. As used herein, a "high touch" region of a room refers to an area of a room where objects of frequent use are arranged. Examples of objects typically found in a high touch zone of a room include but are not limited to desktops, keyboards, telephones, chairs, door and cabinet handles and light switches. Examples of objects in high touch zones of hospital rooms additionally or alternatively include beds, bedside tables, sinks, tray tables and intravenous stands. In some cases, the region between approximately 2 feet and approximately 4 feet from a floor of a room is considered a "high touch" region of a room since objects of frequent use are generally placed in such a region. As such, in some embodiments, disinfection apparatus 12 may be configured to disperse germicide 16 to a region which is between approximately 2 feet and approximately 4 feet from a floor of a room in which the apparatus is arranged.

Examples of configurations of ultraviolet disinfection apparatuses which direct at least some ultraviolet light to a region which is between approximately 2 feet and approximately 4 feet from a floor of a room are disclosed in U.S. patent application Ser. No. 13/156,131 entitled "Ultraviolet Discharge Lamp Apparatus with One or More Reflectors" by Stibich et al. filed on Jun. 8, 2011, which is incorporated by reference as if set forth fully herein. Other configurations of ultraviolet light disinfection apparatuses, however, may be employed for disinfection apparatus 12. In addition, other types of disinfection apparatuses (i.e., disinfection apparatuses configured to generate germicide in a form of a liquid, gas, vapor or plasma) may be configured to disperse a germicide to a region between approximately 2 feet and approximately 4 feet from a floor of a room. In any case, for the reasons set forth above, hollow chamber 20 may, in some embodiments, be arranged between approximately 2 feet and approximately 4 feet from a floor of a room, particularly if disinfection apparatus 12 is specifically configured to direct germicide to such a region. In view thereof, hollow chamber 12 may, in some embodiments, be configured for suspension. For example, hollow chamber 12 may, in some cases, include a latch for hooking on to device, such as an intravenous stand in a hospital room, for instance.

Turning to FIGS. 2 and 3, apparatuses 30 and 35 are respectively shown having disinfection device 12 disposed within hollow chambers 32 and 38. The configurations of apparatuses 30 and 35 differ in the placement of disinfection device 12 within the hollow chambers. In particular, FIG. 2 illustrates apparatus 30 having disinfection device 12 against an interior wall of hollow chamber 32 and FIG. 3 illustrates apparatus 35 having disinfection device 12 disposed apart from the interior walls of hollow chamber 36 by shaft 38. An advantage of having disinfection device 12 apart from the interior walls of hollow chamber is that objects 26 may be more quickly disinfected since germicide 16 will travel a shorter distance and disinfection device 12 may, in some embodiments, disperse more germicide (i.e., the area of disinfection device 12 used to disperse germicide 16 may be larger in apparatus 35 than in apparatus 30). A disadvantage of having disinfection device 12 apart from the interior walls of hollow chamber is that disinfection device 12 may be more susceptible to damage by objects 26 tumbling through the chamber versus being positioned along interior wall of the hollow chamber. It is noted that although FIG. 2 illustrates disinfection device 12 in apparatus 30 as extending from the interior wall of hollow chamber 32, disinfection device 12 may, alternatively, be disposed within the interior wall of hollow chamber 32. In some cases, an exterior surface of disinfection device 12 may be flush with the interior wall of hollow chamber when disposed therein. Such a configuration may be less susceptible to damage from objects 26 tumbling around the chamber versus the configuration shown in FIG. 2.

In any case, apparatuses 30 and 35 are not necessarily restricted to having a single disinfection device disposed therein and, thus, in some cases, may include a plurality of disinfection devices. The plurality of disinfection devices may be configured to generate the same type of germicide, different types of germicides or may be a combination of such devices. Furthermore, the plurality of disinfection devices may all be disposed along the interior walls of the hollow chambers or may be all spaced apart from the interior walls of the hollow chambers. In yet other embodiments, the apparatuses may include at least one disinfection device disposed along an interior wall of a hollow chamber and at least one other disinfection device spaced apart from an interior wall of the hollow chamber.

Hollow chambers 32 and 36 may include many of the characteristics described above for hollow chamber 20 of system 10 depicted in FIG. 1. In particular, hollow chambers 32 and 36 may include loading port 22 and ledges 28 as well as the alternative configurations of such features described above for hollow chamber 20 in reference to FIG. 1. Hollow chambers 32 and 36, however, may differ from hollow chamber 20 in that they need not be perforated and/or be constructed of optically transparent materials. In particular, in some cases, apparatuses 30 and 35 in FIGS. 2 and 3 may be used to simply disinfect objects 26 and, thus, there is no need to disperse germicide 16 exterior to apparatuses 30 and 35 in some embodiments. Consequently, hollow chambers 32 and 36 may, in some case, be void of perforations and/or void of optically transparent materials.

In other cases, however, apparatuses 30 and 35 in FIGS. 2 and 3 may be used to disinfect items exterior to the apparatuses in addition to objects 26 and, thus, hollow chambers 32 and 36 may be perforated in some embodiments and/or include panes of one or more optically transparent materials. In some such cases, hollow chambers 32 and 36 may include moveable and/or removable plugs for placement over the perforations or panes of optical material, offering an option for apparatuses 30 and 35 to disperse germicide 16 exterior to the apparatuses or not. In any case, apparatuses 30 and 35 may include means 24 for providing tumbling action to objects 26 within hollow chambers 32 and 36. The characteristics of means 24 are described above and are not reiterated for the sake of brevity. In addition, apparatuses 30 and 35 may include storage medium 34 having program instructions 14 which are executable by a processor for varying operational parameters of the means 24 while disinfection apparatus 12 is in operation. FIGS. 2 and 3 depict storage medium 34 as a component distinct from apparatuses 30 and 35, but apparatuses 30 and 35 may alternatively serve as a storage medium for program instructions 14.

FIG. 4 illustrates system 40 including hollow chamber 50 with input port 52 configured for coupling to disinfection apparatus 42 such that germicide 44 generated by disinfection apparatus 42 may be transmitted into the hollow interior via the input port when the chamber is coupled to the disinfection apparatus. System 40 differs from system 10 of FIG. 1 and apparatuses of FIGS. 2 and 3 in that disinfection apparatus 42 is configured to generate germicide 44 internally and further includes output port 46 for transmitting germicide 44 to a component coupled thereto, such as hollow chamber 50. In some embodiments, disinfection apparatus 42 may be additionally configured to disperse germicide 44 exterior to the disinfection apparatus, particularly if it is advantageous to disinfect the room, area, or environment in which system 40 is arranged. System 40 further differs from system 10 of FIG. 1 and apparatuses of FIGS. 2 and 3 in that hollow chamber 50 includes input port 52 for coupling to output port 46 of disinfection apparatus 42. It is noted that the configurations of input port 52 and output port 46 may vary widely and, thus, are not limited to their depictions in FIG. 4. Similar to hollow chambers 32 and 36 of FIGS. 2 and 3, hollow chamber 50 may be void of perforations and/or optically transparent materials in some cases, particularly when there is not a desire to disinfect the environment exterior to hollow chamber 50. In other cases, however, hollow chamber 50 may include perforations and/or include panes of one or more optically transparent materials and, in some embodiments, may include moveable and/or removable plugs for closing or blocking the perforations and panes of optically transparent material.

In any case, system 40 may include means 24 for providing tumbling action to objects disposed within hollow chamber 50. The characteristics of means 24 are described above and are not reiterated for the sake of brevity. In addition, system 40 may include program instructions 14 which are executable by a processor for varying operational parameters of the means 24 while disinfection apparatus 12 is in operation. As shown in FIG. 4, program instructions 14 may, in some embodiments, be disposed within disinfection apparatus 42, but in alternative embodiments, program instructions 14 may be disposed with a storage medium distinct from disinfection apparatus 42 such as in hollow chamber 50 or another component of system 40.

A further optional feature which may be included in any of the systems and apparatuses described herein is a means for automatically loading and unloading the hollow chamber. In some of such cases, the hollow chamber may include a loading port and an unloading port. In addition or alternatively, the hollow chamber may be arranged in line with a conveyor belt. In this manner, objects may be loaded on the conveyor belt, automatically led to and dropped into the hollow chamber and, then after treatment by a germicide, automatically removed from the chamber. Such a scenario may be particularly advantageous when a large quantity of objects need to be treated.

A general method for using the systems and apparatuses described herein includes placing one or more objects within a hollow chamber having a means for providing tumbling action to the objects, starting operation of the tumbling means to provide tumbling action to the objects and starting operation of a disinfection apparatus which is in proximity to the hollow chamber, disposed within the hollow chamber, or coupled to the hollow chamber. In some cases, the starting and stopping operations of the tumbling means and disinfection apparatus may be synchronized. In some embodiments, it may be advantageous to at least remotely start and stop the operation of the disinfection apparatus to minimize exposure to the germicide generated by the disinfection apparatus.

It will be appreciated to those skilled in the art having the benefit of this disclosure that this invention is believed to provide germicidal systems and apparatuses having hollow tumbling chambers for disinfecting objects. Further modifications and alternative embodiments of various aspects of the invention will be apparent to those skilled in the art in view of this description. For example, although the aforementioned discussions give specific example of use for disinfecting hospital objects, the systems, apparatuses and methods described herein are not so limited and may be used to disinfect many other types of objects. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system, comprising:

a disinfection apparatus, wherein the disinfection apparatus is configured within the system to project a germicide into an ambient of a room in which the disinfection apparatus is arranged;

a hollow chamber configured and arranged relative to the disinfection apparatus such that the germicide projected into the ambient of the room from the disinfection apparatus is transmitted into an interior cavity of the hollow chamber, wherein the hollow chamber comprises:

a port for loading and/or unloading the interior cavity of the hollow chamber; and a door for closing the port, wherein the door is distinct from and not directly attached to walls of the room; and a means for providing tumbling action to objects placed inside the hollow chamber.

2. The system of claim 1, wherein the hollow chamber is arranged between approximately 2 feet and approximately 4 feet from a floor of a room in which the system is arranged.

3. The system of claim 1, wherein the hollow chamber comprises ledges of different dimensions along walls of the interior cavity.

4. The system of claim 1, wherein the hollow chamber is collapsible.

5. The system of claim 1, further comprising a storage medium having program instructions which are executable by a processor for varying operational parameters of the means for providing tumbling action while the disinfection apparatus is in operation.

6. The system of claim 1, wherein the means for providing tumbling action comprises a rotation motor, pneumatics or a vibrator.

7. The system of claim 5, wherein the program instructions are disposed on or within a support structure of the disinfection apparatus which supports the discharge lamp of the apparatus.

8. The system of claim 1, wherein the means for providing tumbling action comprises an electromechanical, hydraulic or rotational shaft.

9. The system of claim 1, wherein the disinfection apparatus is configured to project the germicide in a form of a mist, a gas, a vapor or a plasma.

10. The system of claim 1, wherein the disinfection apparatus comprises a discharge lamp configured to generate ultraviolet light.

11. The system of claim 10, wherein the hollow chamber comprises an optically transparent material for the ultraviolet light to permeate through.

12. The system of claim 10, wherein the disinfection apparatus comprises a room occupancy sensor for determining whether people are present in a room in which the disinfection apparatus is arranged, wherein the room occupancy sensor is disposed on a support structure of the disinfection apparatus which supports the discharge lamp of the apparatus.

13. The system of claim 12, wherein the room occupancy sensor is a motion detection sensor.

14. The system of claim 12, wherein the room occupancy sensor is a photo recognition sensor.

15. The system of claim 10, wherein the disinfection apparatus comprises wheels to affect portability of the disinfection apparatus, wherein the wheels are disposed on a support structure of the disinfection apparatus which supports the discharge lamp of the apparatus.

16. The system of claim 10, wherein the disinfection apparatus comprises a support structure supporting the discharge lamp, and wherein the discharge lamp extends beyond an exterior surface of the support structure such that ultraviolet light projected from the discharge lamp encircles the disinfection apparatus.

17. The system of claim 10, wherein the discharge lamp is configured to further emit visible light, and wherein the disinfection apparatus comprises an optical filter configured to attenuate a majority amount of the visible light emitted from the discharge lamp.

18. The system of claim 10, wherein the disinfection apparatus comprises a means for moving the discharge lamp relative to a support structure of the disinfection apparatus.

19. The system of claim 18, wherein the means for moving the discharge lamp comprises a means for moving the discharge lamp in and out of the support structure.

20. The system of claim 1, wherein the hollow chamber comprises perforations for the germicide to permeate through.

21. The system of claim 1, wherein the hollow chamber comprises an antimicrobial material.

22. The system of claim 1, further comprising a means for automatically loading and unloading the hollow chamber.

23. The system claim 1, wherein the hollow chamber is configured for suspension.

24. The system of claim 1, wherein the hollow chamber is spaced apart from the disinfection apparatus by less than approximately 5 feet.

25. The system of claim 1, wherein a minority amount of germicide projected into the ambient of the room is transmitted into the interior cavity of the hollow chamber.

26. The system of claim 1, wherein the door is hinged to a sidewall of the hollow chamber.

27. The system of claim 1, wherein the door is a sliding door.

28. The system of claim 1, wherein the door comprises an optically transparent material for the ultraviolet light to permeate through.
29. The system of claim 1, wherein the door comprises perforations for the germicide to permeate through.

30. A disinfection apparatus, comprising:
a hollow chamber comprising:
one or more ports for loading and unloading an interior cavity of the hollow chamber; and
one or more doors for respectively closing each of the one or more ports, wherein exterior sidewalls of the hollow chamber adjoining the one or more ports comprise unobstructed perforations and/or ultraviolet transparent material extending to the interior cavity, and wherein the disinfection apparatus is absent any housing about the hollow chamber;
a device disposed within the interior cavity of the hollow chamber which is configured to generate a germicide which is transmissible through the unobstructed perforations and/or ultraviolet transparent material; and
a means for causing objects placed inside the interior cavity to tumble within the interior cavity.

31. The apparatus of claim 30, wherein the device is disposed within a wall of the interior cavity.

32. The apparatus of claim 30, wherein the device is spaced apart from walls of the interior cavity.

33. The apparatus of claim 30, wherein the device is one of a plurality of devices disposed within the interior cavity which is configured to generate a germicide within the interior cavity.

34. The apparatus of claim 33, wherein one of the plurality of devices is disposed within a wall of the interior cavity, and wherein another of the plurality of devices is spaced apart from walls of the interior cavity.

35. The apparatus of claim 30, wherein the device is a discharge lamp configured to generate ultraviolet light.

36. The apparatus of claim 30, wherein the means for causing objects placed inside the interior cavity to tumble comprises a rotation motor, pneumatics or a vibrator.

37. The apparatus of claim 30, wherein the means for providing tumbling action comprises an electromechanical, hydraulic or rotational shaft.

38. The system of claim 30, wherein the hollow chamber comprises an antimicrobial material.

39. The system of claim 30, further comprising a means for automatically loading and unloading the interior cavity.

40. The system of claim 30, wherein the hollow chamber comprises removable plugs in or over the perforations and/or the ultraviolet transparent material.

41. The system of claim 30, wherein device is configured to generate the germicide in a form of a liquid, gas, vapor or plasma.

42. The disinfection apparatus of claim 30, wherein at least one of the one or more doors is fastened to the hollow chamber.

43. The disinfection apparatus of claim 30, wherein at least one of the one or more doors comprises unobstructed perforations and/or ultraviolet transparent material.

44. A system, comprising:
a disinfection apparatus configured to generate and transmit ultraviolet light through an output port of the disinfection apparatus;
a chamber comprising:
a hollow interior;
a loading port for entry of objects into the hollow interior; and
an input port disposed along an exterior housing of the chamber and extending into the hollow interior, wherein the input port of the chamber and the output port of the disinfection apparatus are directly physically coupled to each other such that ultraviolet light transmitted by the output port passes through the input port into the hollow interior; and
a means for tumbling objects placed inside the chamber.

45. The system of claim 44, wherein the means for providing tumbling action comprises a rotation motor, pneumatics or a vibrator.

46. The system of claim 44, wherein the means for providing tumbling action comprises an electromechanical, hydraulic or rotational shaft.

47. The system of claim 44, wherein the hollow chamber comprises an antimicrobial material.

48. The system of claim 44, further comprising a means for automatically loading and unloading the hollow chamber.

* * * * *